United States Patent [19]
Burk et al.

[11] Patent Number: 5,654,329
[45] Date of Patent: *Aug. 5, 1997

[54] 1,3-BENZODIOXOLE AND 1,2-DIALKOXYBENZENE DERIVATIVES AS OCULAR HYPOTENSIVE AGENTS

[75] Inventors: Robert M. Burk, Laguna Beach; David F. Woodward, El Toro, both of Calif.

[73] Assignee: Allergan, Waco, Tex.

[*] Notice: The term of this patent shall not extend beyond the expiration date of Pat. No. 5,369,127.

[21] Appl. No.: 485,521

[22] Filed: Jun. 7, 1995

Related U.S. Application Data

[60] Division of Ser. No. 345,176, Nov. 28, 1994, Pat. No. 5,523,296, which is a continuation-in-part of Ser. No. 51,104, Apr. 21, 1993, Pat. No. 5,369,127.

[51] Int. Cl.$^6$ .............. A61K 31/36; A61K 31/085; A61K 31/39; A61K 31/165
[52] U.S. Cl. .............. 514/452; 514/438; 514/444; 514/450; 514/461; 514/467; 514/471; 514/532; 514/533; 514/534; 514/544; 514/546; 514/559; 514/570; 514/604; 514/622; 514/646; 514/699; 514/718
[58] Field of Search .............. 514/450, 452, 514/467, 533, 534, 544, 532, 546, 559, 570, 604, 622, 646, 699, 718; 568/442, 329, 330, 308, 592; 562/465; 549/347, 373, 375, 452, 453, 454

[56] References Cited

U.S. PATENT DOCUMENTS

| | | | |
|---|---|---|---|
| 5,066,644 | 11/1991 | Poli et al. | 514/19 |
| 5,091,528 | 2/1992 | Gluchowski | 544/105 |
| 5,151,440 | 9/1992 | Gluchowski | 514/377 |
| 5,369,127 | 11/1994 | Burk et al. | 514/464 |

FOREIGN PATENT DOCUMENTS

| | | | |
|---|---|---|---|
| 0292230 | 11/1988 | European Pat. Off. | C07D 319/08 |
| 3218048 | 1/1983 | Germany | C07D 405/06 |

OTHER PUBLICATIONS

Bito, L. Z., *Applied Pharmacology in the Medical Treatment of Glaucomas*, Drance, S.M. and Neufeld, A.H. eds., New York, Grune & Stratton, 1984 pp. 477–505.

Journal of Medicinal Chemistry, 1975, vol. 18, pp 1094–1098 by Bender et al.

Bito, L. Z., *Biological Protection with Prostaglandins*, Cohen, M.M., ed. Boca Raton Fla. CRC Press Inc., 1985, pp. 231–252.

M.S. Starr, *Exp. Eye Res.* 11, 170–177 (1971).

Barreiro et al, J. Chem Res. Synop., 1, 220–1 (1985) (C.A. 104: 19430c.1986).

*Primary Examiner*—Nicky Chan
*Attorney, Agent, or Firm*—Robert J. Baran; Martin A. Voet; Howard R. Lambert

[57] ABSTRACT

Compounds of the formula

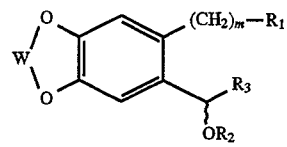

where

W is $(CH_2)_n$ where n is 1 or 2, or n is 0 and W represents lower alkyl groups attached to each oxygen;

m is an integer between 1 and 8;

$R_1$ is COOH or a pharmaceutically acceptable salt thereof, $COOR_4$, $CONR_5R_6$, $CONR_5SO_2R_7$, $CH_2OH$, $CH_2OR_7$, $CH_2O$—$COR_7$, $CH_2O$—$CONR_5R_7$, $CH_2OCOOR_7$, $CH_2NH_2$, $CH_2NR_5R_6$, $CH_2NR_5COR_7$, CHO, $CH(OR_8)_2$, $CH(OR_9O)$, —$COR_{10}$, $CR_{10}(OR_8)_2$, or $CR_{10}OR_9O$, where $R_4$ is an alkyl group of 1 to 10 carbons, or a cycloalkyl group of 5 to 10 carbons, or $R_4$ is phenyl or lower alkylphenyl, $R_5$ and $R_6$ independently are hydrogen, an alkyl group of 1 to 10 carbons, or a cycloalkyl group of 5 to 10 carbons, or phenyl or lower alkylphenyl, $R_7$ is alkyl of 1 to 10 carbons, phenyl or lower alkylphenyl, $R_8$ is lower alkyl, and $R_9$ is divalent alkyl radical of 2–5 carbons, $R_{10}$ is an alkyl or cycloalkyl containing 1 to 5 carbons;

$R_2$ is H, $COR_7$, $R_7$, $CO$—$OR_7$, $CO$—$NR_5,R_7$, $PO(OH)OR_7$, $PO(OR_7)_2$, $POR_7OH$, or $POR_7(OR_7)$;

$R_3$ is lower alkyl, phenyl, lower alkyl or halogen substituted phenyl, phenyl substituted lower alkyl, or heteroaryl substituted lower alkyl, are capable of lowering introaocular pressure in the eye of a mammal.

2 Claims, No Drawings

1,3-BENZODIOXOLE AND 1,2-DIALKOXYBENZENE DERIVATIVES AS OCULAR HYPOTENSIVE AGENTS

CROSS-REFERENCE TO RELATED APPLICATIONS

This patent application is a divisional patent application of U.S. Ser. No. 08/345,176, filed 28 Nov. 1994, now U.S. Pat. No. 5,523,296, which is a continuation-in-part application of U.S. Ser. No. 08/51,104, filed on 21 Apr., 1993, now U.S. Pat. No. 5,369,127.

FIELD OF THE INVENTION

The present invention relates to novel 1,2-benzodioxole and 1,2-dialkoxybenzene derivatives which are active as ocular hypotensive agents. The present invention also relates to methods of administering a pharmaceutical composition containing one or more of said 1,2-benzodioxole and 1,2-dialkoxybenzene derivatives to a mammal for he purpose of lowering the intraocular pressure in the eye of the mammal.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying cause of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical B-adrenoreceptor antagonists have traditionally been the drugs of choice for treating glaucoma.

Prostagladins were earlier regarded as potent ocular hypertensives; however, evidence accumulated in the last two decades shows that some prostaglandins are highly effective ocular hypotensive agents and are suitable for the long-term medical management of glaucoma. (See, for example, M. S. Starr, *Exp. Eye* Res. 11, 170–177, (1971); Bito, L. Z. *Biological Protection with Prostaglandisn* Cohen, M. M., ed., Boca Raton, Fla. CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). There are numerous patent and other disclosures in the prior art describing prostaglandins as ocular hypotensive agents.

In addition to prostaglandins, several other types of chemical compounds are disclosed in the patent and scientific literature as ocular hypotensive agents. For example U.S. Pat. Nos. 5,066,644, 5,091,528, 5,151,440 assigned to the same assignee as the present application, disclose certain oxazoline, thiazoline, imidazoline and 1,4-benzoxazine derivatives as ocular hypotensive agents. An article in Journal of Medicinal Chemistry 1975, Vol. 18, pp 1094–1098 by Bender et al., describe certain heterocyclic homoprostanoids. These compounds, however, are not described to have ocular hypotensive properties.

In J. Chem. Research(s) 1985, 220–221 Barreiro et al. describe the synthesis of 5-[6-(1-hydroxyhexyl)-1,3-benzodioxol-5-yl]-acetic and pentanoic acids as potential anti-inflammatory agents.

The presently known ocular hypotensive agents, however, do not cure or alleviate glaucoma and ocular hypertension in a fully satisfactory manner, and/or without undesirable side effects. For this reason, the search continues in the art for further ocular hypotensive agents, particularly for agents which are more effective, have lesser side-effects or act through a different biological mechanism than presently known ocular hypotensives.

SUMMARY OF THE INVENTION

Novel compounds of the present invention are shown by Formula 1

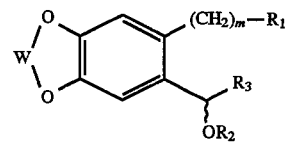

where

W is $(CH_2)_n$ where n is 1 or 2, or n is 0 and W represents lower alkyl groups attached to each oxygen;

m is an integer between 1 and 8;

$R_1$ is COOH or a pharmaceutically acceptable salt thereof, $COOR_4$, $CONR_5R_6$, $CONR_5SO_2R_7$, $CH_2OH$, $CH_2OR_7$, $CH_2O-COR_7$, $CH_2OCONR_5R_7$, $CH_2OCOOR_7$, $CH_2NH_2$, $CH_2NR_5R_6$, $CH_2NR_5COR_7$, CHO, $CH(OR_8)_2$, $CH(OR_9O)$, $-COR_{10}$, $CR_{10}(OR_8)_2$, or $CH_{10}(OR_9O)$, where $R_4$ is an alkyl group of 1 to 10 carbons, or a cycloalkyl group of 5 to 10 carbons, or $R_4$ is phenyl or lower alkyl phenyl, $R_5$ and $R_6$ independently are hydrogen, an alkyl group of 1 to 10 carbons, or a cycloalkyl group of 5 to 10 carbons, or phenyl or lower alkylphenyl, $R_7$ is alkyl of 1 to 10 carbons, phenyl or lower alkylphenyl, $R_8$ is lower alkyl, and $R_9$ is divalent alkyl radical of 2–5 carbons, $R_{10}$ is an alkyl or cycloalkyl containing 1 to 5 carbons;

$R_2$ is H, $COR_7$, $R_7$, $CO-OR_7$, $CO-NR_5R_7$, $PO(OH)OR_7$, $PO(OR_7)_2$, $POR_7OH$, or $POR_7(OR_7)$;

$R_3$ is lower alkyl, phenyl, lower alkyl or halogen substituted phenyl, phenyl substituted lower alkyl, or heteroaryl substituted lower alkyl, with the proviso that when W is $CH_2$, m is 1 or 4, $R_2$ is H, and $R_3$ is n-pentyl then $R_1$ is not COOH.

In another aspect the present invention relates to pharmaceutical compositions containing a active ingredient one or more compounds of the present. invention (or their pharmaceutically acceptable salts).

In still another aspect the present invention relates to methods of administering to a mammal a pharmaceutical composition having as its active ingredient one or more compounds of Formula 1 (or their pharmaceutically acceptable salts) for the purpose of lowering intraocular pressure in the eye of the mammal.

DETAILED DESCRIPTION OF THE INVENTION GENERAL EMBODIMENTS

The present invention relates to novel compounds of Formula 1, and to their use in pharmaceutical compositions and methods for the purpose of lowering intraocular pressure in the eye of a mammal.

Definitions

The term alkyl refers to and covers any and all groups which are known as normal alkyl, branch-chain alkyl and cycloalkyl. Lower alkyl means the above-defined broad definition of alkyl groups having 1 to 6 carbons, and as applicable, 3 to 6 carbons for branch chained and cyclo-alkyl groups.

The term "ester" as used here refers to and covers any compound falling within the definition of that term classically used in organic chemistry. Where the ester is derived from a carboxylic acid corresponding to Formula 1, the term covers the products derived from the treatment of this function with alcohols, preferably with aliphatic alcohols having 1-6 carbons. Where the ester is derived from alcohols corresponding to Formula 1, the term covers compounds of the formula —$CH_2OCOR_7$ where $R_7$ is defined as in connection with Formula 1.

Amide has the meaning classically accorded that term in organic chemistry. In this instance it includes but is not limited to unsubstituted amides and aliphatic mono-and di-substituted amides.

A pharmaceutically acceptable salt may be prepared for any compound used in the method of treatment of this invention, if the compound has a functionality capable of forming such salt, for example an acid functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethanine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention contain one or more chiral centers and therefore exist in enantiomeric and in the event of two or more chiral esters exist in diastereomeric forms. Unless the structural formula or the language of this application specifically designate a particular configuration of a chiral center, the scope of the present invention is intended to cover all such isomers per se, as well as mixtures of diastereomers and racemic mixtures of enantiomers (optical isomers) as well.

General Description of the Preferred Compounds of the Invention

Referring now to the structure shown in Formula 1, compounds are preferred in accordance with the present invention where the symbol W represents normal-lower alkyl groups attached to each oxygen of the benzene ring, or where W represents $(CH_2)_n$ and n is 1.

with regard to the symbol m, compounds are preferred where m is between 3 to 5, and even more preferred where m is 4.

Regarding $R_1$, compounds are preferred in accordance with the present invention where $R_1$ is COOH, $CH_2OH$ or $COOR_4$ where $R_4$ is lower alkyl, particularly methyl.

With regard to the group $R_2$, compounds are preferred in accordance with the present invention where $R_2$ is H, or $COR_7$ where $R_7$ is lower alkyl, particularly methyl.

With regard to the $R_3$ group, compounds are preferred where $R_3$ is lower alkyl, phenyl substituted lower alkyl or heteroaryl substituted lower alkyl. Particularly preferred are compounds where $R_3$ is Ph—$CH_2$—$CH_2$, n-pentyl, 2-thienylethyl or 2-furylethyl.

The most preferred compounds of the invention are shown by the structures of Formula 2 and Formula 3 below.
Compound 1, Formula 2, $R_1=CO_2CH_3$; $R_3=$Ph—$CH_2$—$CH_2$;
Compound 2, Formula 2, $R_1=CH_2OH$; $R_3=$Ph—$CH_2$—$CH_2$;
Compound 3, Formula 2, $R_1=CH_2OH$; $R_3=$n-pentyl;
Compound 4, Formula 3, $R_1=CO_2H$; $R_3=$n-pentyl;
Compound 5, Formula 2, $R_1=CO_2H$; $R_3=$n-pentyl.
Compound 6, Formula 2, $R_1=CH_2OH$; $R_3=$2-thienylethyl.
Compound 7, Formula 2, $R_1=COOH$; $R_3=$2-thienylethyl.

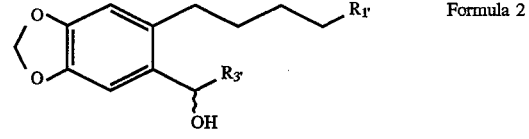

Formula 2

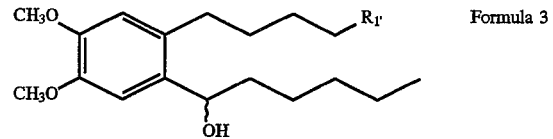

Formula 3

Methods of Administration, Formulations

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v), in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisol and butylated hydroxytoluene.

Other excipient components which may be included in the ophthalmic preparations are chelating agents. The preferred chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop is about 20–35 µl.

Biological Activity

The ability of a pharmaceutical composition which contains a compound of Formula 1 to lower intraocular pressure in the eye of a mammal, can be demonstrated by an assay performed on the eyes of dogs. The assay is described as follows: male and female beagle dogs weighing 10–15 kg had been trained for a minimum of 2 months so that intraocular pressure could be measured without the use of restraining devices. Intraocular pressure was measured by pneumatonometry using applanation tonometers (Alcon). One minute prior to tonometry, 25 µl of proparacaine (Allergan, Irvine Calif.) was applied to minimize ocular discomfort during the procedure. Determination of the effects of the compounds of the invention on intraocular pressure involved administration of 1 to 25 µl of solution of the compound to one eye and an equal volume of vehicle to the contralateral eye as a control.

The effect of the compounds of the invention to lower intraocular pressure in dog eyes, in accordance with the above-described assay is shown in Table 1 with respect to the following compounds:

TABLE 1

| Compound # | Concentration % | Change in IOP (mm of Hg) 6 hours after administr. |
| --- | --- | --- |
| 1 | 0.1 | −1.0 |
| 2 | 0.1 | −1.25 |
| 3 | 0.01 | −3.0 |
| 3 | 0.1 | −4.2 |
| 4 | 0.1 | −1.2 |
| 6 | 0.1 | −1.1 |
| 7 | 0.1 | −1.0 |

In addition, compounds of the invention were also found to inhibit DNA synthesis as observed in an assay where the incorporation of tritium labeled thymidine into Swiss 3T3 cells is measured. The assay is described as follows.

Swiss mouse 3T3 cells were maintained in Dulbecco's modified Eagles medium (DMEM) low glucose and supplemented with 10% fetal bovine serum FBS), 2 mM 1-glutamine and 1% antibiotic-antimycotic 100×. The cultures were incubated in 5% $CO_2$ in air at 37° C. Confluent cultures were trypsinized and plated in quadruplicate cultures for experiments. Cells were plated at $1 \times 10^5$ cells per 35 mm well in DMEM containing 10% FBS in 6-well cluster plates and allowed to become confluent in 3 days. The cells were then made quiescent by washing them with Hank's balanced salt solution (HBSS) and incubating them for 24 hours in DMEM with 0.5% FBS. The cultures were then refed fresh DMEM containing 0.5% FBS and various concentrations of the test compounds. All compounds were dissolved in absolute ethanol, diluted with sterile filtered normal saline and added to the medium so that the final ethanol control cultures were incubated in medium containing 0.01% or less test compounds. The vehicle control cultures were incubated in medium containing 0.01% ethanol in saline. Cultures were incubated for 22 hours before pulse-labeling with [$^3$H]-thymidine ([$^3$H]-TdR).

Pulse-labeling of the cultures consisted of collecting the conditioned, drug-treated or control containing media, then adding 1µ Ci/ml [$^3$H]-TdR and incubating the cultures in the [$^3$H]-TdR containing medium for 5 hours. The cells were then washed with phosphate buffered saline and fixed with 6% trichloroacetic acid (TCA). The cells were scraped from the culture wells and transferred to tubes. Each well was rinsed with 6% TCA and the rinse was added to the appropriate tubes. After centrifugation at 2800 RPM for 20 minutes at room temperature, an aliquot of the supernatant containing unincorporated [$^3$H]-TdR (S1) was transferred to scintillation tubes. Radioactivity was measured by liquid-scintillation counting using Beckman HP cocktail. The remainder S1 supernatant was decanted and 3% perchloric acid (PCA) was added to the cell pellet. The DNA was denatured by placing the tubes in heating blocks at 95° C. for 20 minutes, followed by placing the tubes in an ice bath for 15 minutes. After centrifugation as before, an aliquot of the supernatant containing [$^3$H]-TdR incorporated into DNA (S2) was assayed for radioactivity by scintillation counting.

Analiquot of the remaining S2 supernatant was assayed for quantity of DNA by the diphenylamine method. DNA standards, prepared from salmon testes DNA, and the samples were mixed with the diphenylamine reagent and incubated in a water bath with shaking at 30° C. for 6–24 hours. The diphenylamine reagent was prepared with 1.5% diphenylamine in glacial acetic acid and per 100 ml of the solution, by adding 1.5 ml of concentrated sulfuric acid and 0.5 ml of 1.6% acetaldehyde. Absorbance of the DNA standards and samples was measured in a Beckman Biomek spectrophotometer at 600 nM wavelength.

The data was expressed as CPM ([$^3$H]-TdR incorporated into DNA) per μg DNA and the mean of the quadruplicate samples was obtained for each experiment. The results were presented as per cent of the vehicle control.

Table 2 shows the observed CPM (counts per minute obtained in the assay with the vehicle (control) and with several concentrations of Compound 5. Table 2 also shows the percentage of labeled thymidine incorporation (as measured by CPM) in the samples containing the test compound, as compared to the vehicle control.

TABLE 2

| Compound # | Concentration % | CPM | % of Control |
|---|---|---|---|
| VEHICLE | (Control) | 2601 | 100 |
| Compound 5 | $10^{-7}$ M | 2102 | 82 |
| Compound 5 | $10^{-6}$ M | 1598 | 62 |
| Compound 5 | $10^{-5}$ M | 1454 | 58 |

General Description of Synthetic Procedures

The compounds of the invention can be made by a number of different synthetic chemical pathways. To illustrate the invention, the following detailed description is provided. The synthetic chemist will readily appreciate that the conditions set out here are specific embodiments which can be generalized to obtain any and all compounds described in the present specification.

Scheme 1

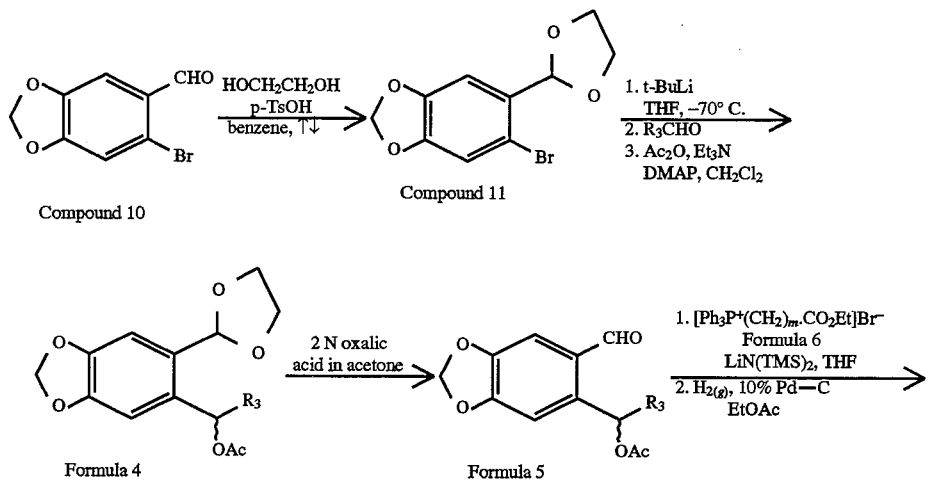

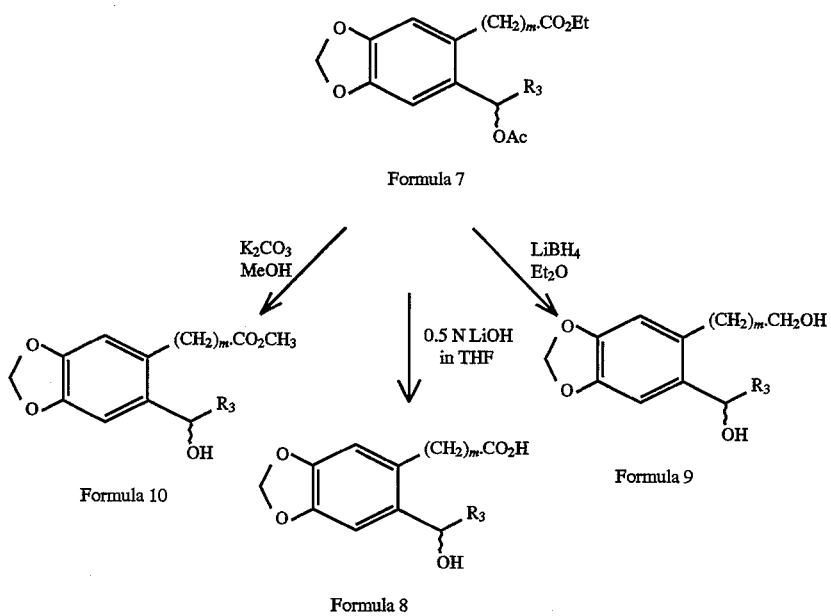

Referring now to Reaction Scheme 1, a synthetic route is disclosed for the preparation of the compounds of the invention where, with reference to Formula 1, W represents $(CH_2)_n$ and n is 1. (1,3-benzodioxole derivatives). The starting material of this scheme is 1,3-benzodioxole-6-bromo-5-carboxalehyde (Compound 10), which can be obtained by bromination of commercially available (Aldrich) 1,3-dioxole-5-carboxaldehyde (also known as piperonal). In accordance with Reaction Scheme 1, the aldehyde function of Compound 10 is protected as an acetal by reaction with ethyleneglycol in the presence of acid. The resulting acetal (Compound 11) is reacted with an aldehyde of the formula $R_3$—CHO in the presence of strong base (such as tertiary butyl lithium), and the resulting secondary alcohol is acetylated to provide a compound of Formula 4. The $R_3$— group of the aldehyde reagent $R_3$—CHO is defined as in connection with Formula 1. (For example, for the preparation of the preferred embodiments the reagent $R_3$CHO is 3-phenylpropionaldehyde, hexanal, 3-(2-thienyl) propionaldehyde and 3-(2-furyl)propionaldehyde). Thereafter, the acetal blocking group is removed, by treatment with acid, from the 5 carboxaldehyde function of the compound of Formula 4, to yield a compound of Formula 5. The compound of Formula 5 has a free aldehyde group which is reacted with a Wittig reagent of Formula 6. The symbol m' of Formula 6 is defined as an integer having the values of 1 to 7, and for this reason compounds of Formula 1 where m is between 2 to 8 can be prepared in accordance with the procedure shown in Reaction Scheme 1. Generally speaking, the Wittig reagent of Formula 6 can be prepared in accordance with synthetic procedures known in the art, for example from the brominated carboxylic acid ester, of the formula $Br(CH_2)_{m'}COOEt$. For example, the Wittig reagent of Formula 6 where m' is 3, can be prepared substantially in accordance with the procedure described by Wernic et al. in Journal of Org. Chem., 1989, Volume 54, 4224–4228 at page 4226. The olephinic product of the Wittig reaction between compounds of Formula 5 and Formula 6 is thereafter hydrogenated to yield a compound of Formula 7. As it will be recognized by those skilled in the art, Formula 7 depicts compounds of Formula 1, where the $R_2$ group is acetyl ($COCH_3$) and $R_1$ is ethyl carboxylate ($C_2Et$). The compounds of Formula 7 can be converted to further compounds of Formula 1, such as into the compounds of Formula 8 where $R_2$ is H and $R_1$ is $CO_2H$, obtainable by saponification, compounds of Formula 9 where $R_2$ is H and $R_1$ is $CH_2OH$, obtainable by reduction with lithium borohydride, and compounds of Formula 10 where $R_2$ is H and $R_1$ is methyl (or other alkyl), obtainable by saponification and trans-esterification.

Reaction Scheme 1A shows an alternative synthetic route to the compounds of the invention, specifically illustrated for compounds where the $R_3$ group is (2-thienyl)ethyl. This synthetic route differs from the synthetic route shown in Reaction Scheme 1 in that the side chain designated $(CH_2)_m R_1$ in Formula 1 is built from the corresponding aldehyde through not one but two Wittig reactions. In the example illustrated in Reaction Scheme 1A a "two carbon fragment" is added in each Wittig reaction, eventually leading to Compound 6 and Compound 7 of the invention. The specific chemical reactions depicted in Reaction Scheme 1A are described in the Specific Examples below.

Reaction Scheme 1A

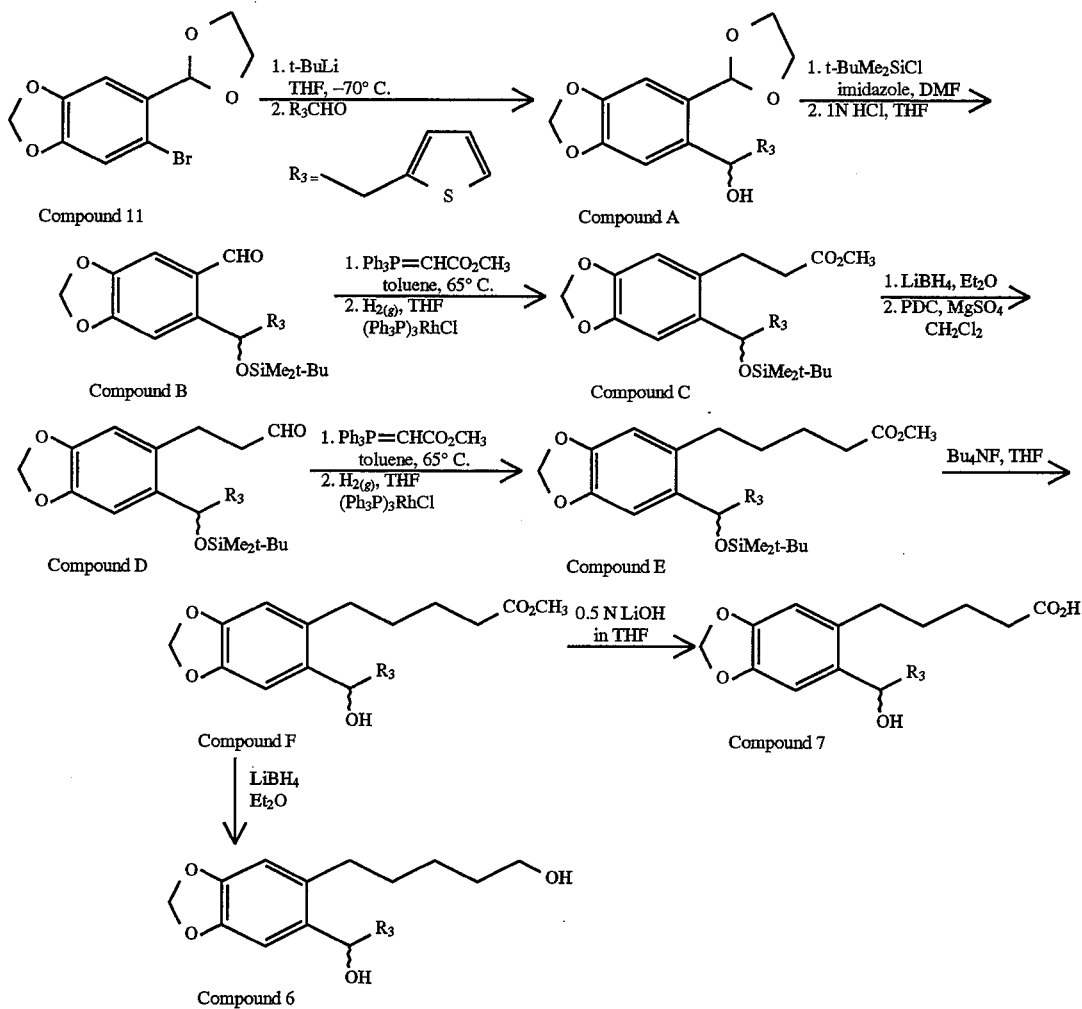

Referring back now to Reaction Scheme 1, generally speaking, the ester functionality of the compounds of Formula 7 can be converted to the amide, sulfonamide, aldehyde, ketone, acetal, ketal, and amino functionalities set forth in connection with Formula 1 by reactions which are per se well known to the practicing organic chemist, are described in standard handbooks and textbooks of organic chemistry, and therefore do not need to be described here.

The compounds of Formula 1 where m=1, cannot be made directly by the Wittig reaction outlined in Reaction Scheme 1. However, these compounds can be obtained by reaction of the aldehyde of Formula 5 with a Grignard or like reagent, followed by such synthetic steps to build the —$CH_2$—$R_1$ side chain on the 1,3-benzodioxole nucleus, which will be apparent to those skilled in the art in light of the present disclosure.

Scheme 2

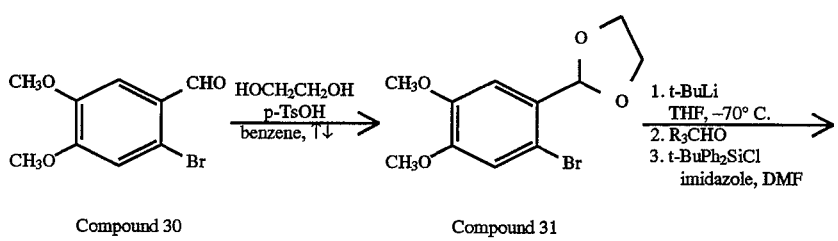

-continued
Scheme 2

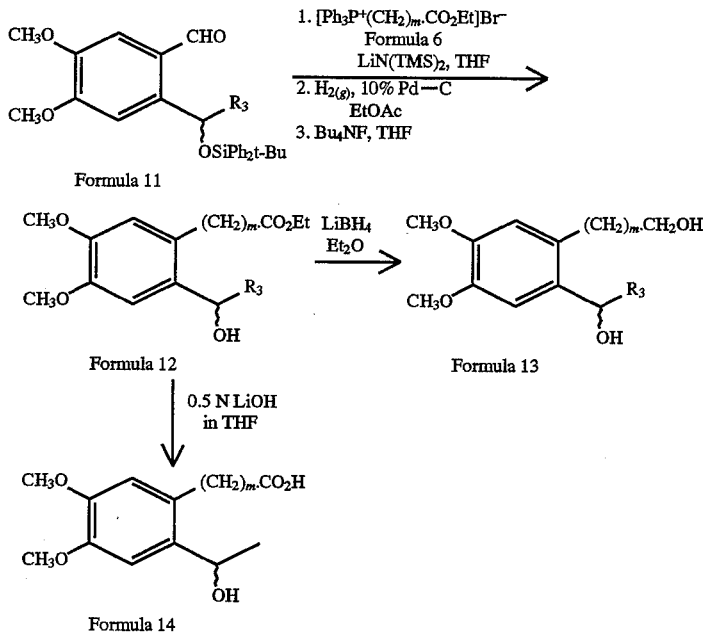
Formula 11, Formula 12, Formula 13, Formula 14

Referring now to Reaction Scheme 2, synthesis of the compounds of the invention is disclosed where in accordance with Formula 1 the symbol W represents two alkyl, specifically methyl groups, attached to the oxygens of the benzene nucleus. The starting material for this synthetic scheme is commercially available (Aldrich) 2-bromo-4,5-dimethoxybenzaldehyde, also known as 6-bromo veratraldehyde, (Compound 30). In accordance with Reaction Scheme 2, the aldehyde group of Compound 30 is protected by reaction with ethylene glycol to obtain the acetal (1,3-dioxolane) derivative Compound 31. Compound 31 is reacted with an aldehyde of the formula $R_3$—CHO in the presence of strong base such as tertiary butyl lithium. The secondary hydroxyl group which is obtained as a result of reaction with the aldehyde is protected by a suitable base-stable protective group, such as the tertiary butyl-diphenylsilyl group, to yield the compound of Formula 11. During the reaction of the secondary alcohol with t-butyl-diphenylsilyl chloride in the presence of mild acid (imidazole) in dimethylformamide as a solvent, the acetal blocking group of the benxaldehyde function is also removed. In the next step the compound of Formula 11 is reacted with the Wittig reagent of Formula 6. The resulting olephinic compound is hydrogenated and the t-butyl-diphenylsilyl blocking group is removed for example by treatment with tetrabutylammonium fluoride in tetrahydrofuran, to yield compounds of Formula 12. As is readily apparent, compounds of Formula 12 are such compounds of Formula 1 where the $R_1$ group is $CO_2Et$, and the $R_2$ group is H. These compounds can be reduced to the primary alcohol ($R_1$ of Formula 1 is $CH_2OH$ as in Formula 13) or can be saponified to yield the free carboxylic acid (as in Formula 14), as described above for the analogous reactions in Reaction Scheme 1. The ethylcarboxylate function of the compounds of Formula 12 can also be converted into the amide, sulfonamide, amine and other functionalities set forth in connection with Formula 1, by reactions well known in the art, as explained above in connection with Reaction Scheme 1.

SPECIFIC EXAMPLES 1,3-Benzodioxole-6-bromo-5-carboxaldehyde (Compound 10)

To a solution of 1,3-benzodioxole-5-carboxaldehyde (piperonal, Aldrich, 30 g., 0.20 mol) in glacial acetic acid (60 mL) was added a solution of bromine (12.0 mL, 0.23 mol) in HOAc (37.5 mL). The resultant solution was stirred for 16 hours and poured into $H_2O$ (1500 mL). The precipitate was removed by vacuum filtration and washed with 0.2N aqueous sodium thiosulfate followed by ice-cold $Et_2O$. The white solid was dissolved in MeOH with heating and upon allowing to cool to 23° C. white needles crystallized. The crystals were collected by vacuum filtration to give 22.4 g (49%) of the title compound.

2-Bromo-4,5-methylenedioxy-5-1,3-dioxolanylbenzene (Compound 11)

A solution of 1,3-benzodioxole-6-bromo-5-carboxaldehyde (Compound 10, 2.0 g, 8.77 mmol), ethylene glycol (2.4 mL, 43.8 mmol) and p-toluene sulfonic acid (83 mg, 0.438 mmol) in benzene (43 mL) was heated to reflux for 16 hours with azeotropical removal of water. The solvent was removed in vacuo and the residue was diluted with EtOAc. After washing with $H_2O$ (2×) and saturated aqueous $NaHCO_3$ the organic portion was dried ($MgSO_4$), filtered and concentrated in vacuo to give 2.28 g (96%) of the title compound acetal (dioxolane) derivative.

$^1$H NMR (300 MHz, $CDCl_3$) δ7.08 (s, 1H), 7.00 (s, 1H), 6.02 (s, 1H), 5.90 (s, 2H), 4.18–4.03 (m, 4H).

(±)-5-(1,3-dioxolanyl)-[6-(1-hydroxy-3-phenypropyl)]-1,3-benzodioxole (Compound 12)

A solution of the aryl bromide (300 mg, 1.10 mmol) in THF (4.4 mL) was cooled to −78° C. and t-BuLi (1.33 mL of a 1.7M solution in pentane, 2.26 mmol) was added dropwise. After 0.5 hours 3-phenylpropionaldehyde (134 mg, 1.00 mmol) in THF (1.8 mL) was added, the reaction was stirred at −78° C. for 0.5 hours, warmed to 23° C. and quenched with saturated aqueous $NH_4Cl$. The aqueous layer was separated and extracted with EtOAc. The combined organic portions were dried ($MgSO_4$), filtered and concentrated in vacuo. Flash column chromatography (silica gel, 3:1 hex/EtOAc) give 182 mg(50%) of the racemic title compound.

(±)-5-(1,3-dioxolanyl)-[6-(1-acetoxy-3-phenylpropyl)]-1,3-benzodioxole (Compound 13)

A solution of (±)-5-(1,3-dioxolanyl)-[6-(1-hydroxy-3-phenylpropyl)]-1,3-benzodioxole (Compound 12, 182 mg, 0.554 mmol), $Et_3N$ ) (0.23 mL, 1.66 mmol), acetic anhydride (78 µl, 0.832 mmol) and dimethylaminopyridine (DMAP, 33.8 mg, 0.277 mmol) in $CH_2Cl_2$(1.0 mL) was stirred at 23° C. for 16 hours. The reaction was diluted with EtOAc and washed with 1N HCl saturated ag. Na $HCO_3$, brine. The organic portion was dried ($MgSo_4$), filtered and concentrated in vacuo. Flash column chromatography (silica gel, 6:1 hex(EtOAc) gave 167 mg (82%) of the title compound.

$^1$H NMR (300 MHz, $CDCl_3$) δ7.31–7.16 (m, 5H), 7.07 (s, 1H), 6.89 (s, 1H), 6.01 (dd, J=4.8, 8.4 Hz, 1H), 5.94 (s, 3H), 4.08–3.88 (m, 4H), 2.80–2.58 (m, 2H), 2.25–2.06 (m, 2H), 2.05 (s, 3H).

(±)-5-[6-(1-acetoxy-3-phenylpropyl)]-1,3-benzodioxole-5-carboxaldehyde (Compound 14)

A solution of (±)-5-(1,3-dioxolanyl)-[6-(1-acetoxy-3-phenylpropyl)]-1,3-benzodioxle (compound 13, 167 mg, 0.451 mmol) in acetone (2.5 mL) was cooled to 0° C. and oxalic acid (2.5 mL of a 2N solution in $H_2O$), 5.01 mmol) was added. The reaction was allowed to warm to room temperature and after 16 hours was neutralized with saturated aqueous $NaHCO_3$ and concentrated in vacuo. The resultant residue was diluted with EtOAc and the organic portion was separated, dried ($MgSO_4$), filtered and concentrated in vacuo. $^1$H NMR indicated formation of the title compound, aldehyde, 127.6 mg (87%).

$^1$NMR (300 MHz, $CDCl_3$) δ10.1 (s, 1H), 7.31–7.15 (m, 6H), 6.99 (s, 1H), 5.51 (dd, J=4.8, 8.4 Hz, 1H), 6.07 (s, 2H), 2.74–2.69 (m, 2H), 2.24–2.08 (m, 2H), 2.09 (s, 3H).

(±)-Ethyl 5-[6-(1-acetoxy-3-phenylpropyl)]-1,3-benzodioxol-5-yl]-pentanoate (Compound 15)

A suspension of (4-carboethoxybutyl)-triphenylphosphonium bromide (4.70 g, 10.27 mmol) in THF (20 mL) was cooled to −70° C. and lithium bis (trimethylsilyl)amide (10.3 mL of a 1.0M solution in THF, 10.27 mmol) was added. After 5 minutes the mixture was warmed to 0° C., stirred 45 minutes, and the bright orange suspension was recooled to −70° C. At this time a solution of (±)-5-[6-(1-acetoxy-3-phenylpropyl)]-1,3-benzodioxole-5-carboxaldehyde (Compound 14, 410 mg, 1.25 mmol) in THF (5 mL) was added dropwise and the reaction was stirred at −70° C. for 16 hours before allowing it to warm to room temperature. The reaction was then quenched with saturated aqueous ammonium chloride. The aqueous layer was separated and extracted (2×) with EtOAc. The combined organics were dried ($MgSO_4$), filtered and concentrated in vacuo. The residue was diluted with hex/EtOAc (6:1), flashed through a plug of silica gel and the filtrate was concentrated in vacuo.

A mixture of the above-obtained crude product and 10% palladium on carbon (100 mg) in EtOAc (4.5 mL) was degassed and purged under an atmosphere of hydrogen gas. After 4 hours the reaction was diluted with EtOAc and filtered through a plug of celite. The filtrate was concentrated in vacuo and the residue was purified by flash column chromatography (silica gel, 4:1 hex/EtOAc) to afford 282 mg (53%) of the title compound.

$^1$NMR (300 Hz, $CDCl_3$) δ7.32–7.16 (m, 5H), 6.85 (s, 1H), 6.59 (s, 1H), 5.91 (s, 2H), 5.87 (dd, J=9.0, 4.5 Hz, 1H), 4.13 (q, 2H), 2.80–1.85 (m, 8H), 2.07 (s, 3H), 1.65–1.34 (m, 4H), 1.26 (t, J=7.5 Hz, 3H).

(±)-Methyl-5-[6-(1-hydroxy-3-phenylpropyl)]-1,3-benzodioxol-5-yl]-pentanoate (compound 1)

A solution of the (±)-ethyl-5-[6-(1-acetoxy-3-phenylpropyl)]-1,3-benzodioxol-5-yl]-pentanoate (compound 15, 45 mg, 0.105 mmol) and potassium carbonate (21.9 mg, 0.158 mmol) in MeOH (0.5 mL) was stirred at 23° C. for 8 hours. The reaction was quenched with saturated aqueous $NH_4Cl$ and extracted with $CH_2Cl_2$. The combined organics were dried ($Na_2SO_4$), filtered and concentrated in vacuo. Flash column chromatography (silica gel, 2:1 hex/EtOAc) of the residue gave 20.4 mg (53%) of the title compound.

$^1$H NMR (300 MHz, $CDCl_3$) δ7.32–7.17 (m, 5H), 7.01 (s, 1H), 6.59 (s, 1H), 5.91 (s, 2H), 4.84–4.81 (m, 1H), 3.67 (s, 3H), 2.82–2.68 (m, 2H), 2.41 (t, J=7.8 Hz, 2H), 2.26 (t, J=7.5 Hz, 2H), 2.15–2.07 (m, 1H), 1.94–1.81 (m, 2H), 1.60–1.42 (m, 4H).

(±)-5-[6-(1-hydroxy-3-phenylpropyl)]-1,3-benzodioxol-5-yl]-pentanoic acid (Compound 16)

A solution of (±)-ethyl-5-[6-(1-acetoxy-3-phenylpropyl)]-1,3-benzodioxol-5-yl]-pentanoate (Compound 15, 43.2 mg, 0.101 mmol) and lithium hydroxide (0.61 mL of a 0.5N aqueous solution, 0.304 mmol) in THF (1.2 mL) was stirred at 23° C. for 16 hours. The reaction was neutralized with 10% citric acid and extracted with EtOAC. The organic portion was dried ($MgSO_4$), filtered and concentrated in vacuo to give 10.5 mg (29%) of the title compound.

$^1$H NMR (300 MHz, $CDCl_3$) δ10.5 (brs, 1H), 7.32–7.20 (m, 5H), 7.01 (s, 1H), 6.59 (s, 1H), 5.92 (s, 2H), 4.83 (dd, J=4.5, 8.4 Hz, 1H), 2.85–2.67 (m, 2H), 2.41 (t, J=7.5 Hz, 2H), 2.30 (t, J=7.2 Hz, 2H), 2.18–1.85 (m, 2H), 1.57–1.46 (m, 4H), 1.26 (brs, 1H).

(±)-5-[6-(1-hydroxy-3-phenylpropyl)]-1,3-benzodioxol-5-yl]-pentanol (Compound 2)

A solution of the (±)-ethyl-5-[6-(1-acetoxy-3-phenyl propyl)]-1,3-benzodioxol-5-yl]-pentanoate (Compound 15, 50 mg, 0.117 mmol) in $Et_2O$ (1.0 mL) was treated with lithium borohydride (5.1 mg, 0.234 mmol) at 23° C. After 16 hours the reaction was quenched with 2N NaOH, stirred for 1hour, and extracted 2× with EtOAc. The combined organics were dried ($MgSO_4$), filtered and concentrated in vacuo. Flash column chromatography (1:1 hex/EtOAc) gave 30.0 mg (80%) of the title compound.

$^1$H NMR (300 MHz $CDCl_3$) δ7.32–7.19 (m, 5H), 7.00 (s, 1H), 6.59 (s, 1H), 5.90 (s, 2H), 4.84 (dd, J=4.4, 8.4 Hz, 1H), 3.60 (t, J=6.4 Hz, 2H), 2.82–2.65 (m, 2H), 2.40 (t, J=7.8 Hz, 2H), 2.13–1.82 (m, 3H), 1.53–1.26 (m, 7H).

(±)-5-(1,3-dioxolanyl)-6-(1-hydroxy)hexyl-1,3-benzodioxole (Compound 20)

Starting with 2-bromo-4,5-methylendioxy-1-(1,3-dioxolanyl)benzene (Compound 11, 1.0 g, 3.67 mmol) and using t-butyl lithium (7.53 mmol) in pentane solution and hexanal (350 mg, 3.50 mmol) following substantially the procedure for the preparation of (±)-5-(1,3-dioxolanyl)-[6-(1-hydroxy-3-phenylpropyl)]-1, 3-benzodioxole (Compound 12) the title compound was obtained in 60 % yield.

(±)-5-(1,3-dioxolanyl)-6-(1-acetoxy)hexyl-1,3-benzodioxole (Compound 21)

Following substantially the procedure described for the preparation of (±)-5-(1,3-dioxolanyl)-[6-(1-acetoxy-3-phenylpropyl)]-1,3-benzodioxole (Compound 13) the title compound was obtained in 84 % yield from the reaction of (±)-5-(1,3-dioxolanyl)-[6-(1-hydroxy-hexyl)]-1,3-benzodioxole (Compound 20, 0.62 g, 2.10 mmol) with acetic anhydride (0.30 ml, 322.9 mg, 3.16 mmol).

$^1$H NMR (300 MHz, CDCl$_3$) δ7.08 (s, 1H), 6.90 (s, 1H), 6.10 (s, 1H), 6.00 (dd, J=5.3, 8.4 Hz, 1H), 5.96 (s, 2H), 4.17–3.99 (m, 4H), 2.04 (s, 3H), 1.89–1.69 (m, 2H), 1.31–1.26 (m, 6H), 0.88 (t, J=6.9 Hz, 3H).

(±)-6-(1-acetoxy)hexyl-1,3-benzodioxole-5-carboxaldehyde (Compound 22)

Following substantially the procedure described for the preparation of (±)-5-[6-(1-acetoxy-3-phenylpropyl)]-1,3-benzodioxole-5-carboxaldehyde (Compound 14) the title compound was obtained in 92 % yield from the reaction of (±)-5-(1,3-dioxolanyl)-[6-(1-acetoxy-hexyl)]-1,3-benzodioxole (Compound 21, 639 mg, 1.90 mmol) with 2N oxalic acid in acetone.

$^1$H NMR (300 MHz, CDCl$_3$) δ10.2 (s, 1H), 7.30 (s, 1H), 6.97 (s, 1H), 6.46 (dd, J=5.4, 8.1 Hz, 1H), 6.06 (s, 2H), 2.09 (s, 3H), 1.92–1.68 (m, 2H), 1.41–1.26 (m, 6H), 0.87 (t, J=6.6 Hz, 3H).

(±)-Ethyl 5-[6-(1-acetoxy)hexyl]-1,3-benzodioxol-5-yl]-pentanoate (Compound 23)

A suspension of (4-carboethoxybutyl)-triphenylphosphonium bromide (6.3 g, 13.83 mmol) in THF (27.6 mL) was cooled to −70° C. and lithium bis trimethylsilyl amide (13.8 mL of a 1.0M solution in THF, 13.83 mmol) was added. After 5 minutes the mixture was warmed to 0° C. for 45 minutes and the bright orange suspension was recooled to −78° C. and a solution of (±)-[6-(1-acetoxy)hexyl]-1,3-benzodioxole-5-carboxaldehyde (Compound 22, 505 mg, 1.73 mmol) in THF (5 mL) was added. The reaction was stirred at −78° C. for 16 hours and allowed to warm to 23° C. where it was quenched with saturated aqueous NH$_4$Cl. The aqueous layer was separated and extracted twice with EtOAc. The combined organics were dried (MgSO$_4$), filtered and concentrated in vacuo. Flash column chromatography (6:1 hex/EtOAc) gave 588.5 mg (87%) of olephinic product.

The crude olephinic product (200 mg, 0.512 mmol) was hydrogenated in EtOAc in the presence of 10% palladium on carbon catalyst substantially in accordance with the procedure described for (±)-ethyl 5-[6-(1-acetoxy-3-phenylpropyl)]-1,3-benzodioxol-5-yl]-pentanoate (Compound 15), to provide the title compound in 98% yield.

$^1$H NMR (300 MHz, CDCl$_3$) δ6.83 (s, 1H), 6.62 (s, 1H), 5.91 (s, 2H), 5.89 (dd, J=5.4, 8.4 Hz, 1H), 4.13 (q, 2H), 2.65–2.59 (m, 2H), 2.34 (t, J=6.9 Hz, 2H), 2.05 (s, 3H), 1.87–1.56 (m, 6H), 1.44–1.26 (m, 6H), 1.26 (t, J=7.2 Hz, 3H), 0.88 (t, J=6.9 Hz, 3H).

(±)-5-[6-(1-hydroxy)hexyl]-1,3-benzodioxol-5-yl]-pentanol (Compound 3)

Following substantially the procedure described for the preparation of (±)-5-[6-(1-hydroxy-3-phenylpropyl)]-1,3-benzodioxol-5-yl]-pentanol Compound 2), the title compound was obtained in 88% yield from the reaction of (±)-ethyl 5-[6-(1-acetoxy-hexyl)]-1,3-benzodioxol-5-yl]-pentanoate (Compound 23, 46.1 mg, 0.117 mmol) with lithium borohydride (10 mg, 0.470 mg).

$^1$H NMR (300 MHz, CDCl$_3$) δ6.98 (s, 1H), 6.62 (s, 1H), 5.92 (s, 2H), 4.89–4.86 (m, 1H), 3.66 (q, 2H), 2.64–2.52 (m, 2H), 1.78–1.23 (m, 16H), 0.89 (t, J=6.6 HZ, 3H).

(±)-Methyl-5-[6-(1-hydroxy)hexyl]-1,3-benzodioxol-5-yl]-pentanoate (Compound 24)

Following Substantially the procedure described for the preparation of (±)-methyl 5-[6-(1-hydroxy-3-phenylpropyl)]-1,3-benzodioxol5-yl]-pentanoate (Compound 1), the title compound was obtained in 79% yield from (±)-ethyl-5-[6-(1-acetoxy)hexyl]-1,3-benzodioxol-5-yl]-pentanoate (Compound 23, 47 mg, 0.119 mmol) by treatment with K$_2$CO$_3$ in methanol.

$^1$H NMR (300 MHz, CDCl$_3$) δ6.97 (s, 1H), 6.60 (s 1H), 5.91 (s, 2H), 4.87–4.83 (m, 1H), 3.66 (s, 3H), 2.66–2.48 (m, 2H), 2.33 (t, J=7.2 Hz, 2H), 1.82–1.26 (m, 13H), 0.88 (t, J=6.6 Hz, 3H).

(±)-5-[6-(1-hydroxy)hexyl]-1,3-benzodioxol-5-yl]-pentanoic acid (Compound 5)

Following substantially the procedure described for the preparation of (±)-5-[6-(1-hydroxy-3-phenylpropyl)]-1,3-benzodioxol-5-yl]-pentanoic acid (Compound 16), the title compound was obtained in 55% yield from (±)-ethyl 5-[6-(1-acetoxy)hexyl)]-1,3-benzodioxol-5-yl]-pentanoate (Compound 23, 50 mg, 0.127 mmol) by treatment with LiOH in THF.

$^1$H NMR (300 MHz, CDCl$_3$) δ10.6 (5, 1H), 6.97 (s, 1H), 6.61 (s, 1H), 5.92 (s, 2H), 4.86 (dd, J=5.1, 7.8 Hz, 1H), 2.68–2.48 (m, 2H), 2.38 (t, J=7.2 Hz, 2H), 1.72–1.26 (m, 13H), 0.88 (t, J=6.9 Hz, 3H).

1-Bromo-2-(1,3-dioxolanyl)-4,5-dimethoxybenzene (Compound 31)

Following substantially the procedure described for the preparation of 2-Bromo-4,5-methylenedioxy-1-1,3-dioxolanylbenzene (Compound 11), the title compound was obtained in 97% yield from commercially available (Aldrich) 2-bromo-4,5-dimethoxybenzaldehyde (Compound 30, 5.0 g, 0.02 mol) by reaction with ethylene glycol (6.33 g, 0.102 mol) in toluene (80 ml) in the presence of p-toluenesulfonic acid (190 mg, 0.001 mol).

$^1$H NMR (300 MHz, CDCl$_3$) δ7.12 (s, 1H), 7.02 (s, 1H), 6.00 (s, 1H), 4.21–4.07 (m, 4H), 3.90 (s, 3H), 3.89 (s, 3H).

(±)-1-[1,3-dioxolanyl)-2-(1-hydroxy-hexyl )-4,5-dimethoxybenzene (Compound 32)

Following substantially the procedure described for the preparation of (±)-5-(1,3-dioxolanyl)-6-(1-hydroxy)hexyl)1,3-benzodioxole (Compound 20), the title compound was obtained in 37% yield from the reaction of 1-bromo-2-(1,3-dioxolanyl)-4,5-dimethoxybenzene (Compound 31, 5.56 g, 0.0193 mol) with hexanal (1.93 g, 0.0193 mol) in THF in the presence of t-butyl lithium (0.0396 mol) in pentane solution.

(±)-2-(t-butyldiphenylsilyloxy)hexyl-4,5-dimethoxybenzene-1-carboxaldehyde (Compound 33)

A solution of (±)-1-(1,3-dioxolanyl)-2-(1-hydroxy)hexyl-4,5-dimethoxybenzene (Compound 32, 2.2 g, 7.09 mmol), imidazole (0.97 g, 14.19 mmol) and t-butylchlorodiphenylsilane (2.8 mL, 10.64 mmol) in DMF (14 mL) was stirred at 23° C. for 72, hours. The reaction was diluted with Et$_2$O and washed with 1N HCl, H$_2$O and brine. The organic portion was dried (MgSO$_4$), filtered and concentrated in vacuo. Flash column chromatography (silica gel, 5:1 hex/EtOAc) gave 3.52 g (99%) of the title compound wherein absence of the acetal blocking group to give the free aldehyde function was unexpected.

¹H NMR (300 MHz, CDCl₃) δ9.98 (s, 1H), 7.74–7.63 (m, 3H), 7.48–7.20 (m, 8H), 7.03 (s, 1H), 5.41–5.38 (m, 1H), 3.92 (s, 3H), 3.88 (s, 3H), 1.83–1.56 (m, 2H), 1.20–1.09 (m, 6H), 1.06 (s, 9H), 0.79 (t, J=7.2 Hz, 3H).

(±)-Ethyl 5-[2-(1-hydroxy)hexyl-4,5-dimethoxy)phenyl]-1-pentanoate (Compound 34)

(±)-2-(t-Butyldiphenylsilyloxy)hexyl)-4,5-dimethoxybenzene-1-carboxaldehyde (Compound 33, 441 mg, 0.875 mmol) was reacted with (4-carboethoxybutyl)triphenylphosphonium bromide (3.25 g, 7.10 mmol) in THF (14 mL) and lithium bis trimethylsilyl amide (6.58 mmol) substantially in accordance with the procedure described in connection with the preparation of (±)-ethyl 5-[6-(1-acetoxy)hexyl-1,3-benzodioxol-5-yl]-pentanoate (Compound 23), to yield the crude olefinic (alkane) product in 84% yield.

A mixture of the alkene (443.5 mg, 0.736 mmol) and 10% Pd-C (150 mg) in EtOAc (6.0 mL) was degassed and purged under an atmosphere of hydrogen gas. After 16 hours the reaction mixture was filtered through a plug of celite and the filtrate was concentrated in vacuo to give the saturated product as a light yellow oil.

The oil was diluted with THF (8.0 mL) and Bu₄NF (2.2 mL of a 1.0M solution in THF, 2.2 mmol) was added. After 48 hours the reaction mixture was diluted with EtOAc and washed with H₂O (2×). The organic portion was dried (MgSO₄), filtered and concentrated in vacuo. Flash column chromatography (silica gel, 2:1 hex/EtOAc) gave 112 mg (42%) of the title compound.

¹H NMR (300 MHz, CDCl₃) δ7.01 (s, 1H), 6.62 (s, 1H), 4.90–4.87 (m, 1H), 4.13 (q, 2H) 3.88 (s, 3H), 3.87 (s, 3H), 2.70–2.55 (m, 2H), 2.34 (t, J=7.2 Hz, 2H), 1.77–1.23 (m, 13H), 1.26 (t, J=7.2 Hz, 3H), 0.89 (t, J=5.1 Hz, 3H).

(±)-5-[2-(1-hydroxy)hexyl-4,5-dimethoxyphenyl)]-1-pentanol (Compound 35)

Lithium borohydride (0.13 mL of a 2.0M solution in THF, 0.256 mmol) was added to a solution of (±)-ethyl 5-[2-(1-hydroxy)hexyl-4,5-dimethoxyphenyl]-1-pentanoate (Compound 34, 47 mg, 0.128 mmol) in Et₂O (1.5 mL) at 23° C. After 16 hours the reaction was quenched with 2N NaOH and extracted with CH₂Cl₂. The combined organics were dried (Na₂SO₄), filtered and concentrated in vacuo. Flash column chromatography (silica gel, 1:1 hex/EtOAc) gave 34.7 mg (84% of the title compound.

¹H NMR (300 MHz, CDCl₃) δ7.00 (s, 1H), 6.62 (s, 1H), 4.91–4.87 (m, 1H), 3.87 (s, 3H), 3.86 (s, 3H), 3.64 (t, J=6.3 Hz, 2H), 2.67–2.50 (m, 2H), 1.98 (brs, 1H), 1.82–1.26 (m, 15H), 0.88 (t, J=6.6 Hz, 3H).

(±)-5-[2-(1-Hydroxy)hexyl-4,5-dimethoxyphenyl]-1-pentanoic acid (Compound 4)

Lithium hydroxide (0.48 mL of a 0.5N aqueous solution, 0.240 mmol) was added to a solution of (±)-ethyl 5-[2-(1-hydroxy)hexyl-4,5-dimethoxyphenyl]-1-pentanoate (Compound 34, 44 mg, 0.120 mmol) in THF (0.96 mL) at 23° C. After 16 hours the reaction was acidified with 10% citric acid and extracted with CH₂Cl₂. The organic portion was dried (Na₂SO₄), filtered and concentrated in vacuo. Flash column chromatography (silica gel, 100% EtOAc) gave 39.7 mg (98%) of the acid.

¹H NMR (300 MHz, CDCl₃) δ11.6 (s, 1H), 6.99 (s, 1H), 6.61 (s, 1H), 4.88 (dd, J=5.3, 7.8 Hz, 1H), 3.87 (s, 3H), 3.86 (s, 3H), 2.69–2.50 (m, 2H), 2.38 (t, J=6.6 Hz, 2H), 1.82–1.29 (m, 13H), 0.88 (t, J=6.6 Hz, 3H).

(±)-5-(1,3-Dioxolanyl)-[6-(1-hydroxy-3-(2-thienyl)propyl)]-1,3-benzodioxole. (Compound A)

By a procedure similar to that shown for Compound 12 above (±)-5-(1,3 -dioxolanyl)-[6-(1-hydroxy-3-(2-thienyl)propyl)]-1,3-benzodioxole was prepared from compound 11 (1.37 g, 5.02 mmol) using tert-butyllithium (6.0 mL of a 1.7M solution in pentane, 10.30 mmol) 3-(2-thienyl)propionaldehyde (469 mg, 3.35 mmol) and THF (20 mL) in 69% yield. ¹H NMR (300 MHz, CDCl₃) δ7.13 (d, J=5.1 Hz, 1H), 7.05 (s, 2H), 6.93 (dd, J=3.6, 5.1 Hz, 1H), 5.83 (d, J=3.6 Hz, 1H), 5.97 (s, 2H), 5.83 (s, 1H), 5.00–5.03 (m, 1H), 3.95–4.12 (m, 4H), 2.92–3.10 (m, 2H), 2.41 (d, J=1.8 Hz, 1H), 2.06–2.23 (m, 2H).

(±)-5-[[6-(1-t-butyldimethylsilyloxy-3-(2-thienyl)propyl]-1,3-benzodioxolyl]carboxaldehyde (Compound B)

A solution of (±)-5-(1,3-dioxolanyl)-[6-(1-hydroxy-3-(2-thienyl)propyl)]-1,3-benzodioxole (Compound A, 770 mg, 2.30 mmol), imidazole (314 mg, 4.61 mmol) and t-butyldimethysilyl chloride (521 mg, 3.46 mmol) in DMF (4.6 mL) was stirred at 23° C. for 16 hours. The reaction mixture was diluted with Et₂O and washed with 1N HCl, saturated aqueous NaHCO₃ and brine. The organic portion was dried (MgSO₄), filtered and the filtrate concentrated in vacuo to give 562 mg (55%) of the crude silyl ether as an oil.

The residue was diluted with a 1:1 mixture of 1N HCl:THF (12.0 mL) and stirred for 1 hour at 23° C. The reaction mixture was extracted with EtOAc (2×) and the combined organics were washed with saturated aqueous NaHCO₃ brine, dried (MgSO₄), filtered and concentrated in vacuo. Flash column chromatography (silica gel, 9:1 hex/EtOAc) gave a 99% yield of the title compound. ¹H NMR (300 MHz, CDCl₃) δ10.13 (s, 1H), 7.28 (s, 1H), 7.16 (s, 1H), 7.11 (d, J=5.4 Hz, 1H), 6.90 (dd, J=3.6, 5.4 Hz, 1H), 6.78 (d, J=3.6 Hz, 1H), 6.07 (d, J=5.1 Hz, 2H), 5.54–5.56 (m, 1H), 2.94 (t, J=8.4 Hz, 2H), 2.04–2.07 (m, 2H), 0.91 (s, 9H), 0.07 (s, 3H), −0.13 (s, 3H).

(±)-Methyl-3-[[6-(1-t-butyldimethysilyloxy-3-(2-thienyl)propyl)]-1,3-benzodioxolyl]propanoate (Compound c)

A mixture of (±)-5-[[6-t-butyldimethylsilyloxy-3-(2-thienyl)propyl)]-1,3-benzodioxolyl]carboxaldehyde (Compound B, 671 mg, 1.66 mmol) and methyl (triphenylphosphoranylidene)acetate (2.22 g, 6.64 mmol) in toluene was stirred at 23° C. for 96 hours. The reaction mixture was concentrated in vacuo. The residue was diluted with Et₂O, filtered under vacuum and the filtrate was concentrated in vacuo. Purification by flushing through a plug of silica gel (19:1 hex/EtOAc) gave 730 mg (99%) of intermediary ene-ester as an oil.

The oil obtained above, Wilkinson's catalyst (700 mg) and THF (9.0 mL) were thoroughly degassed and purged under an atmosphere of hydrogen gas. After 16 hours the reaction mixture was concentrated in vacuo and the residue was purified by flash column chromatography (silica gel, 19:1 hex/EtOAc) to give 666.3 mg (87%) of the title compound, ¹H NMR (300 MHz, CDCl₃) δ7.10 (d, J=5.4 Hz, 1H), 6.99 (s, 1H), 6.91 (dd, J=3.6, 5.4 Hz, 1H), 6.78 (d, J=3.6 Hz, 1H), 6.58 (s, 1H), 5.92 (d, J=6.3 Hz, 2H), 4.88–4.92 (m, 1H), 3.67 (s, 3H), 2.78–2.96 (m, 4H), 2.50 (t, J=7.8 Hz, 2H), 1.85–2.04 (m, 2H), 0.91 (s, 9H), 0.05 (s, 3H), −0.17 (s, 3H).

(±)-3-[[6-(1-t-butyldimethylsilyloxy-3-(2-thienyl)propyl)]-1,3-benzodioxolyl]propionaldehyde (Compound D)

Lithium borohydride (32.6 mg, 1.49 mmol) was added to a solution of the (±)-methyl-3-[[6-(1-t- butyldimethylsilyloxy-3-(2-thienyl)propyl)]-1,3-benzodioxolyl]propanoate (Compound 6, 666 mg, 1.44 mmol) in Et$_2$O (4.5 mL). After 12 hours the reaction was quenched with 1N NaOH, stirred 1 hour, and then extracted with EtOAc. The organic portion was dried (MgSO$_4$), filtered and concentrated in vacuo to give a viscous oil.

The crude alcohol obtained above was diluted with CH$_2$Cl$_2$ (7.5 mL) then MgSO$_4$ (840 mg), crushed 4 A sieves (840 mg) and pyridinium dichromate (840 mg, 2.23 mmol) were added. After 16 hours the reaction mixture was diluted with Et$_2$O and filtered through celite. The filtrate was concentrated in vacuo and the residue was purified by flash column chromatography (silica gel, 9:1 hex/EtOAc) to afford 317 mg (51%) of the title compound. $^1$H NMR (300 MHz, CDCl$_3$) δ9.60 (s, 1H), 7.11 (d, J=5.1 Hz, 1H), 6.99 (s, 1H), 6.93 (dd, J=3.3, 5.1 Hz, 1H), 6.79 (d, J=3.3 Hz, 1H), 6.59 (s, 1H), 5.93 (d, J=6.4 Hz, 2H), 4.88–4.92 (m, 1H), 2.76–2.97 (m, 4H), 2.52 (t, J=7.6 Hz, 2H), 1.84–2.06 (m, 2H), 0.91 (s, 9H), 0.05 (s, 3H), −0.18 (s, 3H).

(±)-Methyl-5-[[6-(1-t-butyldimethylsilyloxy-3-(2-thienyl)propyl)]-1,3-benzodioxolyl]pentanoate (Compound E)

By a procedure similar to that described for Compound C above, the title compound was prepared by condensation of (±)3-[[6-(1-t-butyldimethylsilyloxy-3-(2-thienyl)propyl)]-1,3-benzodioxolyl]propionaldehyde (Compound D, 317 mg, 0.733 mmol) with methyl(triphenylphosphoranylidene)acetate (382 mg, 1.14 mmol) in toluene (3.0 mL) followed by hydrogenation with Wilkinson's catalyst (350 mg) in THF (3.0 mL) in 50% overall yield. $^1$H NMR (300 MHz, CDCl$_3$) δ7.12 (d, J=5.1 Hz, 1H), 6.99 (s, 1H), 6.92 (dd, J=4.5, 5.1 Hz, 1H), 6.80 (d, J=4.4 Hz, 1H), 6.57 (s, 1H), 5.91 (dd, J=1.5, 9.9 Hz, 2H), 4.85–4.89 (m, 1H), 3.68 (s, 3H), 2.96 (t, J=8.1 Hz, 2H), 2.42–2.49 (m, 2H), 2.31 (t, J=6.9 Hz, 2H), 1.78–2.06 (m, 2H), 1.48–1.67 (m, 4H), 0.92 (s, 9H), 0.05 (s, 3H), −0.18 (s, 3H).

(±)-Methyl-5-[[6-(1-hydroxy-3-(2-thienyl)propyl)]-1,3-benzodioxolyl]pentanoate (Compound F)

Tetrabutylammonium fluoride (0.58 mL of a 1.0M solution in THF, 0.58 mmol) was added to (±)-methyl-5-[[6-(1-t-butyldimethylsilyloxy-3-(2-thienyl)propyl)]-1,3-benzodioxolyl]pentanoate (Compound E, 178 mg, 0.36 mmol) in THF (4.5 mL). After 16 hours the reaction was diluted with EtOAc and washed with H$_2$O. The organic portion was dried (MgSO$_4$) filtered and concentrated in vacuo. Flash column chromatography (silica gel, 2:1 hex/EtOAc) gave 135 mg (99%) of the title compound. $^1$H NMR (300 MHz, CDCl$_3$) δ7.14 (d, J=5.1 Hz, 1H), 7.01 (s, 1H), 6.93 (dd, J=3.3, 5.1 Hz, 1H), 6.83 (d, J=3.3 Hz, 1H), 6.60 (s, 1H), 5.92 (s, 2H), 4.88–4.91 (m, 1H), 3.67 (s, 3H), 2.96–3.03 (m, 2H), 2.43–2.49 (m, 2H), 2.29 (t, J=6.9 Hz, 2H), 1.88–2.20 (m, 2H), 1.80 (d, J=3.0 Hz, 1H), 1.44–1.66 (m, 4H).

(±)5-[[6-(1-hydroxy-3-(2-thienyl)propyl)-1,3-benzodioxolyl]pentanol (Compound 6)

Lithium borohydride (2.1 mg, 0.096 mmol) was added to a solution of (±)-methyl-5-[[6-(1-hydroxy-3-(2-thienyl)propyl]-1,3-benzodioxolyl]pentanoate (Compound F, 36.0 mg, 0.096 mmol) in Et$_2$O (2.0 mL) at 23° C. After 12 hours the reaction was quenched with 1N NaOH, stirred 1 hour, and extracted with EtOAc. The organic portion was dried (MgSO$_4$), filtered and concentrated in vacuo. Purification by flash column chromatography (silica gel, 2:1 hex/EtOAc) provided 32.6 mg (98%) of the title compound. $^1$H NMR (300 MHz, CDCl$_3$) δ7.14 (d, J=5.5 Hz, 1H), 7.01 (s, 1H), 6.93 (dd J=3.3, 5.5 Hz, 1H), 6.84 (d, J=3.3 Hz, 1H), 6.61 (s, 1H), 5.92 (s, 2H), 4.88–4.92 (m, 1H), 3.63 (t, J=5.7 Hz, 2H), 2.97–3.03 (m, 2H), 2.43–2.49 (m, 2H), 1.84–2.20 (m, 3H), 1.26–1.59 (m, 7H).

(±)-5-[[6-(1-hydroxy-3-(2-thienyl)propyl)]-1,3-benzodioxolyl]pentanoic acid (Compound 7)

A mixture of (±)-methyl-5-[[6-(1-hydroxy-3-(2-thienyl)propyl-1,3-benzodioxolyl]pentanoate Compound F, 35 mg, 0.093 mmol) and lithium hydroxide (0.37 mL of a 0.5N solution in H$_2$O, 0.186 mmol) in THF (0.74 mL) was stirred at 23° C. for 16 hours. The mixture was acidified with 1N HCl and extracted with EtOAc. The organic portion was dried (MgSO$_4$) filtered and concentrated in vacuo. Flash column chromatography (silica gel, 100% EtOAc) afforded 33.3 mg (99%) of the title compound. $^1$H NMR (300 MHz, CDCl$_3$) δ12.0 (brs, 1H), 7.14 (d, J=5.1 Hz, 1H), 7.00 (s, 1H), 6.93 (dd, J=3.3, 5.1 Hz, 1H), 6.83 (d, J=3.3 Hz, 1H), 6.59 (s, 1H), 5.91 (s, 2H), 4.87–4.92 (m, 1H), 2.97 (t, J=5.4 Hz, 2H), 2.43–2.47 (m, 2H), 2.32 (t, J=6.9 Hz, 2H), 1.86–2.18 (m, 2H), 1.44–1.64 (m, 5H).

What is claimed is:

1. A method for lowering intraocular pressure in the eye of a mammal, which comprises administering to the mammal a pharmaceutical composition containing a pharmaceutically acceptable excipient and an effective amount of a compound having the formula

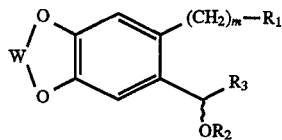

where

W is (CH$_2$)$_n$ where n is 1 or 2, or n is 0 and W represents lower alkyl groups attached to each oxygen;

m is an integer between 1 and 8;

R$_1$ is COOH or a pharmaceutically acceptable salt thereof, COOR$_4$, CONR$_5$R$_6$, CONR$_5$SO$_2$R$_7$, CH$_2$O—CONR$_5$R$_7$, CH$_2$OCOOR$_7$, CH$_2$NH$_2$, CH$_2$NR$_5$R$_6$, CH$_2$NR$_5$COR$_7$, CHO, CH(OR$_8$)$_2$, CH(OR$_9$O), —COR$_{10}$, CR$_{10}$(OR$_8$)$_2$, or CR$_{10}$(OR$_9$O) where R$_4$ is an alkyl group of 1 to 10 carbons, or a cycloalkyl group of 5 to 10 carbons, or R$_4$ is phenyl or lower alkylphenyl, R$_5$ and R$_6$ independently are hydrogen, an alkyl group of 1 to 10 carbons, a cycloalkyl group of 5 or 10 carbons, phenyl or lower alkylphenyl, R$_7$ is alkyl of 1 to 10 carbons, phenyl or lower alkylphenyl, R$_8$ is lower alkyl, and R$_9$ is divalent alkyl radical of 2–5 carbons, R$_{10}$ is an alkyl or cycloalkyl containing up to 5 carbons;

R$_2$ is H, COR$_7$, R$_7$, CO—OR$_7$, CO—NR$_5$R$_7$, PO(OH)OR$_7$, PO(OR$_7$)$_2$, POR$_7$OH, or POR$_7$(OR$_7$);

R$_3$ is lower alkyl, phenyl, lower alkyl or halogen substituted phenyl, phenyl substituted lower alkyl or thienyl or furyl substituted lower alkyl.

2. The method of claim 1 wherein the pharmaceutical composition is adapted for topical administration.

* * * * *

UNITED STATES PATENT AND TRADEMARK OFFICE
CERTIFICATE OF CORRECTION

PATENT NO. : 5,654,329            Page 1 of 2
DATED : August 5, 1997
INVENTOR(S) : Burk et al It is certified that error appears in the above-indentified patent and that said Letters Patent is hereby corrected as shown below:

Column 1, line 20; delete "he" and insert in place thereof --the--

Column 2, line 57; delete "$CH_{10}(OR_9O)$" and insert in place thereof -- $CH(OR_9O)$ --.

Column 3, line 7; delete "a" and insert in place thereof --as--

Column 3, line 8; delete "present." and insert in place thereof --present--

Column 4, line 17; delete "with" and insert in place thereof --With--

Column 7, line 11; delete "Analiquot" and insert in place thereof --An aliquot--

Column 8, line 3; delete "minute" and insert in place thereof --minute)--

Column 9, line 6; delete "carboxalehyde" and insert in place thereof --carboxaldehyde--

Column 10, line 39; delete "$(C_2Et)$" and insert in place thereof --$(CO_2Et)$--

UNITED STATES PATENT AND TRADEMARK OFFICE
CERTIFICATE OF CORRECTION

PATENT NO. : 5,654,329

DATED : August 5, 1997

INVENTOR(S) : Burk et al

It is certified that error appears in the above-indentified patent and that said Letters Patent is hereby corrected as shown below:

Column 18, line 7; delete "Substantially" and insert in place thereof --substantially--

Column 18, line 9; delete "benzodioxol5" and insert in place thereof --benzodioxol-5--

Column 18, line 50; delete "hexyl)1" and insert in place thereof --hexyl)-1--

Column 19, line 15; delete "his" and insert in place thereof --bis--

Signed and Sealed this

Third Day of February, 1998

BRUCE LEHMAN

*Attest:*

*Attesting Officer*     *Commissioner of Patents and Trademarks*